United States Patent [19]
Davis et al.

[11] Patent Number: 5,906,637
[45] Date of Patent: May 25, 1999

[54] DISPOSABLE ELASTIC THERMAL UNIAXIAL JOINT WRAP

[75] Inventors: Leane Kristine Davis, Milford; Daniel Louis Barone, Cincinnati; William Robert Ouellette, Cincinnati; Ronald Dean Cramer, Cincinnati, all of Ohio

[73] Assignee: The Procter & Gamble Company, Cincinnati, Ohio

[21] Appl. No.: 08/916,083

[22] Filed: Aug. 21, 1997

[51] Int. Cl.[6] .................................................. A61F 7/00
[52] U.S. Cl. ..................... 607/108; 607/108; 607/112; 607/114; 607/111; 165/46; 126/204
[58] Field of Search ...................... 165/46; 607/108–114; 383/901; 126/204

[56] References Cited

U.S. PATENT DOCUMENTS

| | | | |
|---|---|---|---|
| Re. 32,026 | 11/1985 | Yamashita et al. | 126/263 |
| 1,727,897 | 9/1929 | Myers et al. | 602/62 |
| 3,425,487 | 2/1969 | Tucker | 165/42 |
| 3,575,782 | 4/1971 | Hansen | 161/141 |
| 4,062,995 | 12/1977 | Korpman | 428/134 |
| 4,300,562 | 11/1981 | Pieniak | 128/237 |
| 4,333,782 | 6/1982 | Pieniak | 156/164 |
| 4,414,970 | 11/1983 | Berry | 128/156 |
| 4,522,863 | 6/1985 | Keck et al. | 428/196 |
| 4,525,407 | 6/1985 | Ness | 428/138 |
| 4,573,991 | 3/1986 | Pieniak et al. | 604/385 A |
| 4,575,097 | 3/1986 | Branningan et al. | 128/402 |
| 4,586,506 | 5/1986 | Nangle | 128/403 |
| 4,606,964 | 8/1986 | Wideman | 428/152 |
| 4,628,932 | 12/1986 | Tamoa | 128/402 |
| 4,652,487 | 3/1987 | Morman | 428/138 |
| 4,671,267 | 6/1987 | Stout | 128/156 |
| 4,688,572 | 8/1987 | Hubbard et al. | 128/402 |
| 4,720,415 | 1/1988 | Vander Wielen et al. | 428/138 |
| 4,748,975 | 6/1988 | Yashima | 602/60 |
| 4,753,241 | 6/1988 | Brannigan et al. | 128/380 |
| 4,789,699 | 12/1988 | Kieffer et al. | 524/271 |

(List continued on next page.)

FOREIGN PATENT DOCUMENTS

| | | | |
|---|---|---|---|
| SHO 58-37075 | 3/1983 | Japan | C09K 5/00 |
| HEI 6-315498 | 11/1994 | Japan | A61F 7/08 |
| HEI 7-67907 | 3/1995 | Japan | A61F 7/08 |
| HEI 7-124192 | 5/1995 | Japan | A61F 7/08 |
| HEI 7-194642 | 8/1995 | Japan | A61F 7/08 |

OTHER PUBLICATIONS

U.S. application No. 08/777,853, Cramer et al., filed Dec. 31, 1996.
U.S. application No. 08/496,565, Ouellette et al., filed Jun. 29, 1995.
U.S. application No. 08/754,947, Burkett et al., filed Nov. 21, 1996.
U.S. application No. 08/623,752, White, filed Mar. 29, 1996.
U.S. application No. 08/680,472, Ouellette et al., filed Jul. 15, 1996.
U.S. application No. 08/775,210, Cramer et al., filed Dec. 31, 1996.
U.S. application No. 08/916,094, Davis et al., filed Aug. 21, 1997.
U.S. application No. 08/915,831, Barone et al., Aug. 21, 1997.

*Primary Examiner*—Bob Nasser
*Assistant Examiner*—Michael Astorino
*Attorney, Agent, or Firm*—Douglas C. Mohl; Loy M. White; T. David Reed

[57] ABSTRACT

The present invention relates to disposable elastic thermal uniaxial joint wraps having an elastic laminate structure formed from a polymeric mesh and two fabric carrier layers, and one or more heat cells, preferably one or more thermal packs comprising a plurality of individual heat cells, wherein heat is applied to specific areas of the user's body, preferably for the knee and/or elbow, preferably for pain relief. These wraps provide good conformity to user's body to deliver consistent, convenient and comfortable heat application.

36 Claims, 5 Drawing Sheets

U.S. PATENT DOCUMENTS

| | | | |
|---|---|---|---|
| 4,805,620 | 2/1989 | Meistrell | 128/402 |
| 4,834,741 | 5/1989 | Sabee | 604/385.2 |
| 4,841,958 | 6/1989 | Ersfeld et al. | 128/90 |
| 4,856,502 | 8/1989 | Ersfeld | 128/90 |
| 4,886,063 | 12/1989 | Crews | 128/403 |
| 4,957,795 | 9/1990 | Riedel | 428/74 |
| 4,977,011 | 12/1990 | Smith | 428/152 |
| 4,984,584 | 1/1991 | Hansen et al. | 128/898 |
| 5,027,801 | 7/1991 | Grim | 128/80 H |
| 5,046,479 | 9/1991 | Usui | 126/204 |
| 5,086,761 | 2/1992 | Ingram | 602/26 |
| 5,139,477 | 8/1992 | Peters | 602/26 |
| 5,148,804 | 9/1992 | Hill et al. | 128/402 |
| 5,151,092 | 9/1992 | Buell et al. | 750/775 |
| 5,156,793 | 10/1992 | Buell et al. | 264/288.8 |
| 5,167,897 | 12/1992 | Weber et al. | 264/288.8 |
| 5,179,944 | 1/1993 | McSymytz | 128/403 |
| 5,187,005 | 2/1993 | Stahle et al. | 428/252 |
| 5,209,801 | 5/1993 | Smith | 156/161 |
| 5,230,701 | 7/1993 | Meyer et al. | 602/76 |
| 5,334,446 | 8/1994 | Quantrille et al. | 428/284 |
| 5,352,497 | 10/1994 | Patel | 428/34.1 |
| 5,366,492 | 11/1994 | Ueki | 607/114 |
| 5,393,599 | 2/1995 | Quantrille et al. | 428/284 |
| 5,395,399 | 3/1995 | Rosenwald | 107/108 |
| 5,399,153 | 3/1995 | Caprico, Jr. et al. | 602/62 |
| 5,415,624 | 5/1995 | Williams | 602/2 |
| 5,451,201 | 9/1995 | Prengler | 602/26 |
| 5,470,639 | 11/1995 | Gessner et al. | 428/152 |
| 5,496,357 | 3/1996 | Jensen et al. | 607/108 |
| 5,496,358 | 3/1996 | Rosenwald | 607/108 |
| 5,503,908 | 4/1996 | Faass | 428/198 |
| 5,728,057 | 3/1998 | Ouellette et al. | 602/62 |
| 5,741,318 | 4/1998 | Ouellette et al. | 607/108 |

DISPOSABLE ELASTIC THERMAL UNIAXIAL JOINT WRAP

TECHNICAL FIELD

The present invention relates to disposable elastic thermal uniaxial joint wraps having an elastic laminate structure formed from a polymeric mesh and two fabric carrier layers, and one or more heat cells, such that heat is applied to specific areas of the user's body, preferably for pain relief. More particularly, the present invention relates to disposable elastic thermal uniaxial joint wraps, preferably for the knee and/or elbow, having an elastic laminate structure and one or more thermal packs comprising a plurality of individual heat cells providing good conformity to user's body to deliver consistent, convenient and comfortable heat application.

BACKGROUND OF THE INVENTION

A common method of treating temporary or chronic pain is by application of heat to the afflicted area. Such heat treatments are used as a means of therapy for conditions which include aches, stiffness in muscles and joints, nerve pain, rheumatism and the like.

The human knee and elbow are two of the most vulnerable joints of the human body to overstress injury. While elastic compression bandages have been used to help stabilize knee movement during injury healing, heating pads, whirlpools, hot towels, and hydrocollators have been commonly used to apply heat to the knee to relieve the pain of knee injury. These pain relieving and stabilization devices, however, typically provide either one function or the other, but not both.

In general, the beneficial therapeutic effects from the administration of heat diminish after the heat source is removed. Therefore, depending on the temperature, it is desirable to provide a sustained heat source to the afflicted area for as long as possible to achieve the desired therapeutic benefits. Many of the current heating devices which require the thermal source to be replenished, such as the devices mentioned above or those employing reusable thermal packs containing water and/or microwaveable gels, are inconvenient to use on a regular and extended basis because the heat energy may not be immediately available when needed or released in a controllable manner.

Disposable heat packs based on iron oxidation, such as those described in U.S. Pat. Nos. 4,366,804, 4,649,895, 5,046,479 and Re.32,026, have been developed, however, such devices have proven not totally satisfactory. Many of these devices are bulky, cannot maintain a consistent and controlled temperature, and/or have unsatisfactory physical dimensions which hinder their effectiveness, and hence, deliver inconsistent, inconvenient and/or uncomfortable heat application to the body.

Proper positioning of the thermal energy also may not be maintainable during knee or elbow flexure with current heating devices. Elastic laminate structures have previously been used in a variety of products including elastic absorbent structures such as sweat bands, bandages, diapers, and incontinence devices. Several methods for producing these laminate structures, such as those disclosed in U.S. Pat. Nos. 4,522,863, 4,606,964, and 4,977,011, also currently exist. However, while these elastic laminate structures may be suitable for the purposes for which they were intended, they have strands which protrude on cut sides of the structure such that they can be a source of irritation when worn next to the body. Further, if an elastic laminate structure having a large modulus value (i.e., the ratio of stress to strain) is desired, elastic strands having a large cross-sectional area are generally required. Large strands of this type, however, can produce a rough or "nubby" feeling when placed in contact with the body.

The present inventors have developed disposable elastic thermal uniaxial joint wraps which maintain proper positioning during use on a user's knee or elbow while providing both compression and thermal energy in a controlled and sustainable manner. These wraps comprise one or more thermal bonded elastic laminate structures, which preferably comprise two carrier layers and an elastic member integrally thermal bonded therebetween, and one or more heat cells, preferably one or more thermal packs, wherein each thermal pack comprises a plurality of individual heat cells, which typically comprise an exothermic composition, preferably comprising a specific iron oxidation chemistry and specific physical dimensions and fill characteristics, spaced apart and fixedly attached across the thermal pack. The thermal bonded elastic laminate structures, when incorporated into the knee and/or elbow wraps of the present invention, substantially reduce delamination of the composite structure of the wraps during use, substantially reduce the rough and "nubby" feeling and irritation caused by strands protruding from cut edges, and provide the knee and/or elbow wraps with excellent conformity to the user's knee and/or elbow for uniform heat coverage and enhanced comfort.

It is therefore an object of the present invention to provide disposable elastic uniaxial joint wraps having excellent conformity to the user's knee and/or elbow for uniform heat coverage and enhanced comfort, which comprise one or more thermal bonded elastic laminate structures and one or more heat cells, which provide a controlled and sustained temperature and which reach their operating temperature range relatively quickly.

It is a further object of the present invention to provide disposable elastic uniaxial joint wraps, which comprise one or more thermal bonded elastic laminate structures, which comprise two carrier layers and an elastic member integrally bonded therebetween and one or more thermal packs comprising a plurality of individual heat cells. Such elastic laminate structures substantially reduce delamination of the composite structure of the wraps, substantially reduce the rough or "nubby" feeling and irritation caused by strands protruding from cut edges, and provide consistent, convenient, and comfortable heat application while deterring easy access to the heat cell contents.

It is a still further object of the present invention to provide disposable elastic uniaxial joint wraps, preferably for the knee and/or elbow, which comprise one or more thermal bonded elastic laminate structures, which preferably comprise two carrier layers and an elastic member integrally bonded therebetween, and one or more thermal packs having a unified structure of at least one continuous layer of semirigid material, which has different stiffness characteristics over a range of temperatures, and a plurality of individual heat cells, spaced apart and fixedly attached across the unified structure of the thermal pack providing good overall drapability while maintaining sufficient rigidity to maintain structural support of the heat cells and to prevent unacceptable stretching of the continuous layer or layers during processing or use.

These objectives and additional objectives will become readily apparent from the detailed description which follows.

SUMMARY OF THE INVENTION

The disposable elastic thermal uniaxial joint wraps of the present invention, comprise a piece of flexible material having an outer surface, a body-facing surface, a first end, a second end, a body portion, a first strap portion, a second strap portion, wherein at least one of body portion, first strap portion, and second strap portion comprise an elastic portion stretchable along a longitudinal axis of the piece of flexible material, and one or more heat cells comprising an exothermic composition, which preferably substantially fills the available cell volume within the cell.

The elastic portion of the flexible material comprises a laminate structure having a first carrier layer, a second carrier layer, and a mesh disposed between the first and second carrier layers. The mesh is preferably elastic in at least one direction and comprises a plurality of first strands intersecting a plurality of second strands, wherein first and second strands have softening temperatures, at an applied pressure, such that at least 10% of first strands are integrally bonded to first and second carrier layers by application of a bonding pressure at the softening temperature of the first strands.

The piece of flexible material has a length great enough to encircle a user's knee and/or elbow such that the first and second ends overlap when the flexible material is in a relaxed or stretched state. The first and second ends comprise a reclosable fastening means, preferably a hook and loop fastening system, for attaching the first end to said piece of flexible material in order to hold said piece of flexible material around the user's knee or elbow. More preferably, the fastening means comprises a two-part fastening means which additionally comprises a plurality of hook members which engage loop fibers of a landing zone attached to, or part of, the piece of flexible material in order to adjust the wrap to a variety of user sizes and to attain a comfortable level of elastic tension.

The piece of flexible material preferably comprises an aperture therein intended to be aligned with the user's patella (knee) or olecranon (elbow) to establish a convenient locating point for wrapping the uniaxial joint wrap around the user's knee or elbow. The piece of flexible material preferably comprises a slit extending substantially longitudinally from the aperture for enabling the piece of flexible material to stretch transverse to the longitudinal axis at the aperture in order to accommodate bending of the user's knee or elbow.

The elastic thermal uniaxial joint wraps preferably comprise one or more thermal packs, preferably embedded in the piece of flexible material, to apply thermal energy to the user's knee or elbow. The thermal pack or packs comprise a unified, structure comprising at least one continuous layer of a coextruded film, preferably comprising a first side of polypropylene and a second side comprising a low melt temperature polymer, which has different stiffness characteristics over a range of temperatures. The thermal pack or packs further comprise a plurality of individual heat cells which provide a controlled and sustained temperature and which reach their operating temperature range quickly. The heat cells are spaced apart and fixedly attached within each thermal pack. Each thermal pack provides good drapability while maintaining sufficient rigidity to maintain structural support of the heat cells and to prevent unacceptable stretching of the continuous layer or layers during processing or use, providing consistent, convenient and comfortable heat application. Preferably, the heat cells comprise a mixture of powdered iron, powdered carbon, water, and metal salt, which when exposed to oxygen, provides heat for several hours.

The present invention further comprises methods for making disposable elastic thermal uniaxial joint wraps, wherein the elastic laminate structure is formed prior to assembly of the flexible material and comprises the steps of:

a) providing a first carrier layer;

b) providing a second carrier layer;

c) providing a mesh disposed between the first and second carrier layers, having a plurality of first strands intersecting a plurality of second strands, the first and second strands having softening temperatures at an applied pressure, wherein the softening temperature of the second strands, at the applied pressure, is greater than the softening temperature of the first strands at the applied pressure;

d) heating the mesh to the softening temperature of first strands and less than the softening temperature of the second strands;

e) applying a bonding pressure to the first strands; and f) integrally bonding from about 10% to about 100% of the first strands to the first and second carrier layers.

All percentages and ratios used herein are by weight, and all measurements made at 25° C., unless otherwise specified.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements and wherein:

DETAILED DESCRIPTION OF THE INVENTION

Figure 1:
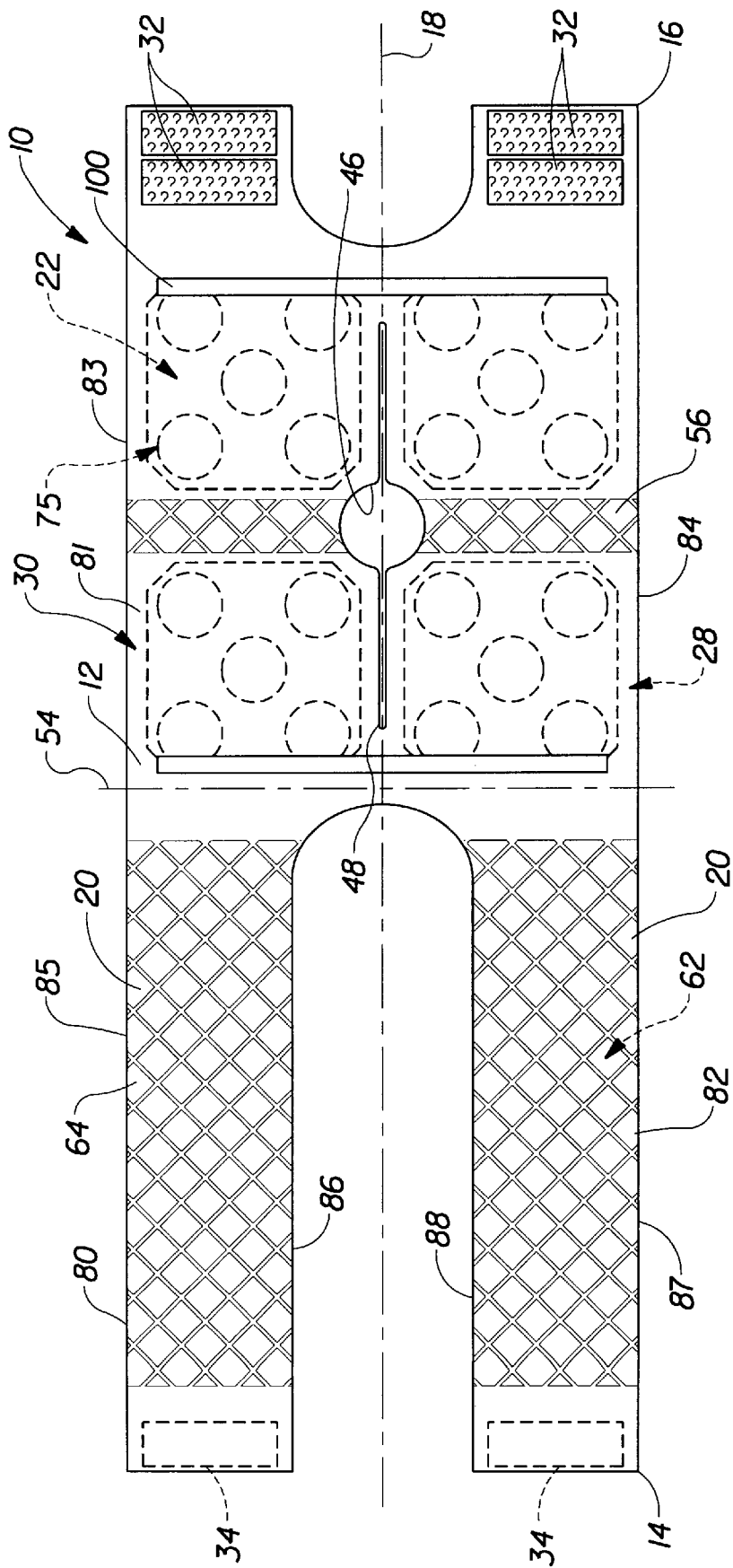
FIG. 1 is a top plan view of a preferred embodiment of the present invention, showing the preferred pattern of heat cells and/or thermal pack(s)

The disposable elastic thermal uniaxial joint wraps of the present invention comprise at least one elastic portion of flexible material having at least one elastic laminate structure, wherein the laminate structure comprises at least one elastic member integrally thermal bonded between a first carrier layer and second carrier layer, and at least one heat cell. Preferably the disposable elastic thermal knee wrap of the present invention comprises at least one elastic laminate structure and one or more thermal packs having at least one continuous layer of a material, which exhibits specific thermophysical properties and a plurality of individual heat cells spaced apart and fixedly attached across the thermal pack, providing good overall drapability while maintaining sufficient rigidity to maintain structural support of the heat cells and to prevent unacceptable stretching of the continuous layer or layers during processing or use. The disposable elastic thermal uniaxial joint wrap of the present invention, provides consistent, convenient, and comfortable heat application, and an excellent conformity to the user's knee or elbow, while retaining sufficient rigidity to deter easy access to the heat cell contents.

The term "disposable", as used herein, means that, while the elastic thermal wraps of the present invention may be stored in a resealable, substantially air impermeable container and reapplied to the user's body as often as required for the relief of pain, they are intended to be thrown away, i. e., deposited in a suitable trash receptacle, after the heat source, i. e., the heat cell(s) or thermal pack(s), has been fully expended.

The term "heat cells", as used herein, means a unified structure, comprising an exothermic composition, preferably a specific iron oxidation chemistry, enclosed within two layers, wherein at least one layer may be oxygen permeable, capable of providing long lasting heat generation with improved temperature control, and having specific physical dimensions and fill characteristics. These heat cells can be used as individual heating units, or in a thermal pack comprising a plurality of individual heat cells which can also be easily incorporated into disposable body wraps, pads, and the like. Body wraps incorporating heat cells or thermal packs adapt to a wide variety of body contours, thus providing consistent, convenient, and comfortable heat application.

The term "direct compaction", as used herein, means a dry powder mixture is blended, compressed, and formed into pellets, tablets, or slugs without the use of typical wet binders/solutions to adhere the particulate(s) together. Alternatively, the dry powder mixture is blended and roll compacted or slugged, followed by milling and screening, creating directly compacted granules. Direct compaction may also be known as dry compaction.

The term "fill volume", as used herein, means the volume of the particulate composition or the compacted, water-swelled, heating element in the filled heat cell.

The term "void volume", as used herein, means the volume of the cell left unfilled by the particulate composition or the compacted heating element in a finished heat cell.

The term "cell volume", as used herein, means the fill volume plus the void volume of the heat cell.

The term "continuous layer or layers", as used herein, means one or more layers of a material which may be uninterrupted or partially, but not completely, interrupted by another material, holes, perforations, and the like, across its length and/or width.

The term "semirigid material", as used herein, means a material which is rigid to some degree or in some parts and exhibits a toughness to maintain structural support of the heat cells in an unsupported format, and/or to prevent unacceptable stretching of structures of the material during processing or use and/or to deter easy access to the heating element contents while still maintaining good overall drape characteristics when heated.

Figure 2:
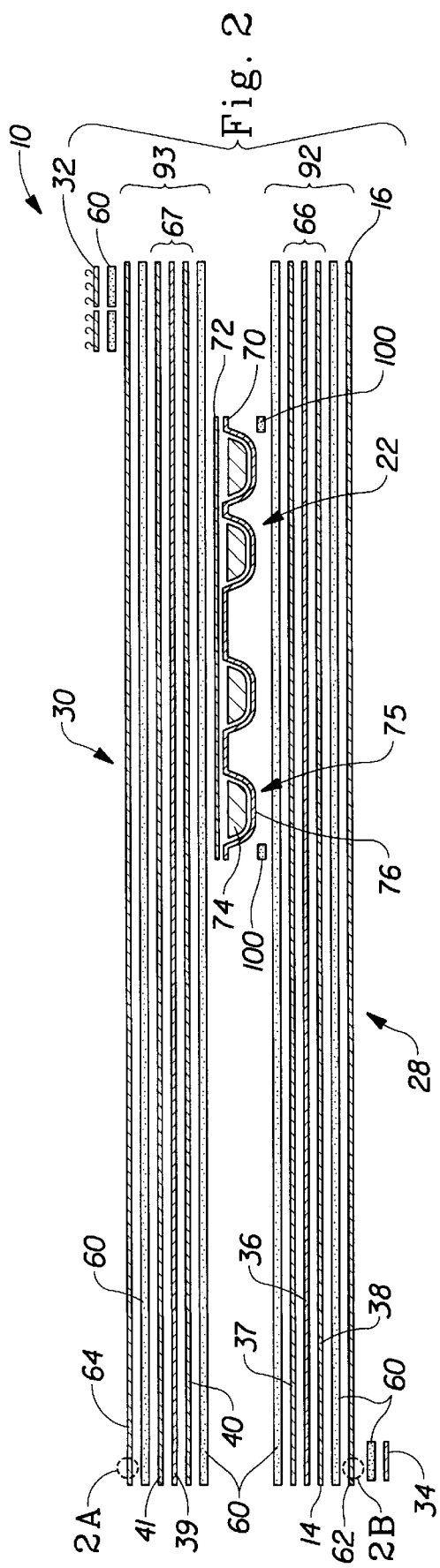
FIG. 2 is a sectioned side elevation view of FIG. 1, disclosing the laminate structure of the present invention.
Figure 2B:
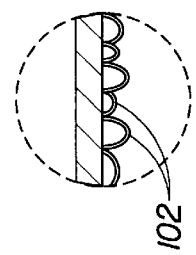
Figure 2A:
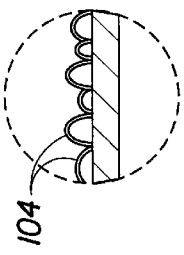

Referring now to the drawings, and more particularly to FIGS. 1 and 2, there is shown a preferred embodiment of the present invention, which provides a disposable elastic thermal uniaxial joint wrap, and is generally indicated as 10. Wrap 10 comprises a piece of flexible material 12 having a longitudinal axis 18.

Flexible material 12 comprises a first end 14 and a second end 16, a body portion 81, and preferably a first strap portion 80 and second strap portion 82, wherein at least one of body portion 81, first strap portion 80, and second strap portion 82 comprise elastic portion 20 capable of being stretched along longitudinal axis 18. Flexible material 12 has a length, when in a relaxed or stretched state, as measured in a direction parallel to longitudinal axis 18 from first end 14 to second end 16, which is great enough to encircle a user's knee or elbow such that first end 14 overlaps second end 16. Flexible material 12 has a body-facing material 62, comprising body-facing surface 28, and an outer surface material 64, comprising outer surface 30, extending from first end 14 to second end 16.

As used herein, "elastic" refers to that property of a material whereby the material, when subjected to a tensile force, will stretch or expand in the direction of the force and will essentially return to its original untensioned dimension upon removal of the force. More specifically, the term "elastic" is intended to mean a directional property wherein an element or structure has a recovery to within about 10% of its original length Lo after being subjected to a percent strain $\epsilon_\%$ of greater than 50%. As used herein, percent strain $\epsilon_\%$ is defined as:

$$\epsilon_\% = [(L_f - L_o)/L_o]*100$$

Where
 $L_f$=Elongated Length
 $L_o$=Original Length

For consistency and comparison, the recovery of an element or structure is preferably measured 30 seconds after release from its elongated length $L_f$. All other elements or structures will be considered inelastic if the element or structure does not recover to within about 10% of its original length $L_o$ within 30 seconds after being released from a percent strain $\epsilon_\%$ of 50%. Inelastic elements or structures would also include elements or structures which fracture and/or permanently/plastically deform when subjected to a percent strain $\epsilon_\%$ of 50%.

Referring now to FIGS. 1–4, elastic portion 20 of flexible material 12 comprises a first elastic member 36. First elastic member 36 is preferably thermally bonded to first carrier layer 37 and second carrier layer 38 prior to assembly of flexible material 12 to form first thermal bonded elastic laminate 66. First thermal bonded elastic laminate 66 is then fixedly attached to body-facing material 62, by hot melt adhesive layer 60 to form body-facing laminate 92.

Preferably, elastic portion 20 of flexible material 12 further comprises a second elastic member 39. Second elastic member 39 is preferably thermally bonded to third carrier layer 40 and fourth carrier layer 41 prior to assembly of flexible material 12 to form second thermal bonded elastic laminate 67. Second thermal bonded elastic laminate 67 is then fixedly attached to outer surface material 64, by hot melt adhesive layer 60 to form outer surface laminate 93. Body-facing laminate 92 is then fixedly attached to outer surface laminate 93 with one or more individual heat cells 75, preferably one or more thermal packs 22, interposed therebetween, by hot melt adhesive layer 60, to form wrap 10.

Figure 3:
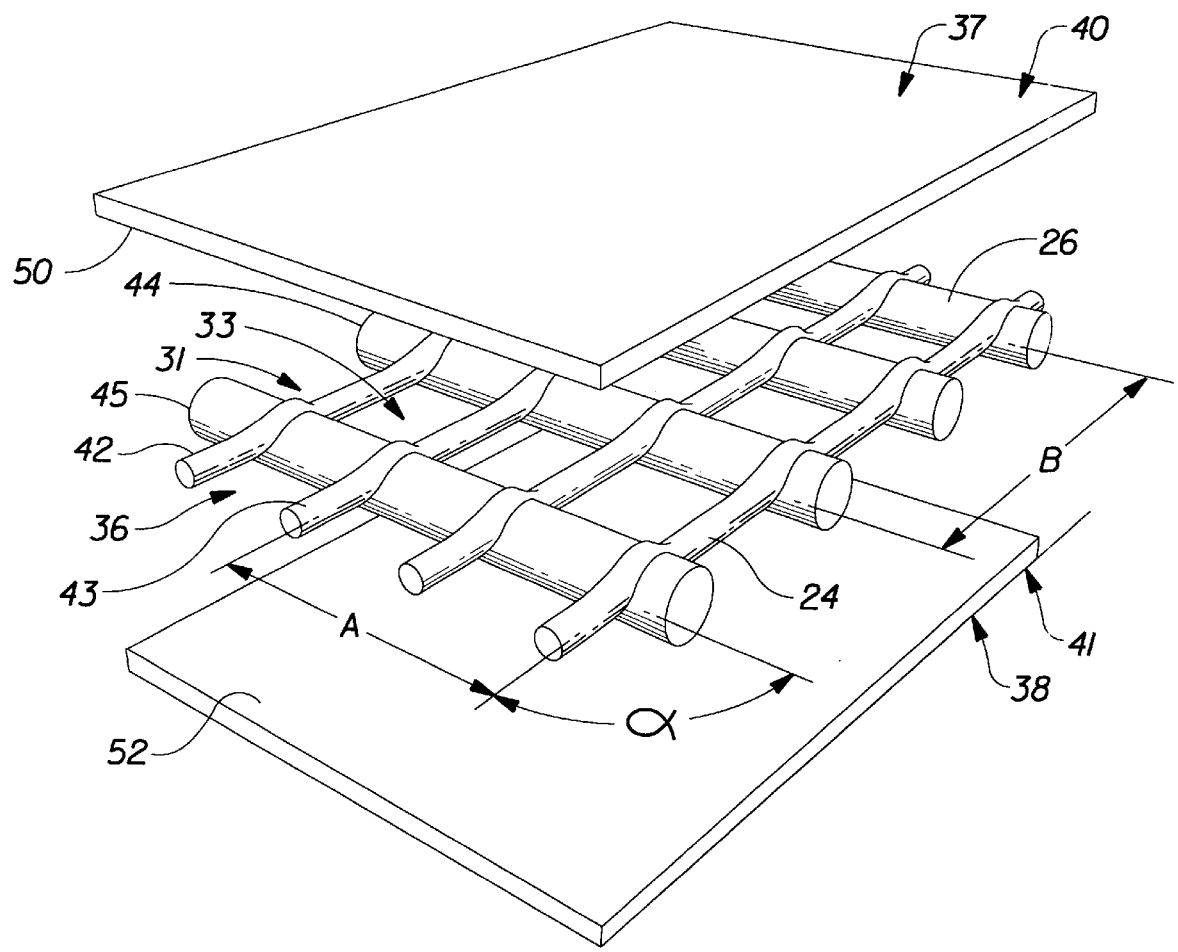
FIG. 3 is an exploded view of a mesh and first and second carrier layer prior to being formed into a laminate structure, made in accordance with the present invention.
Figure 4:
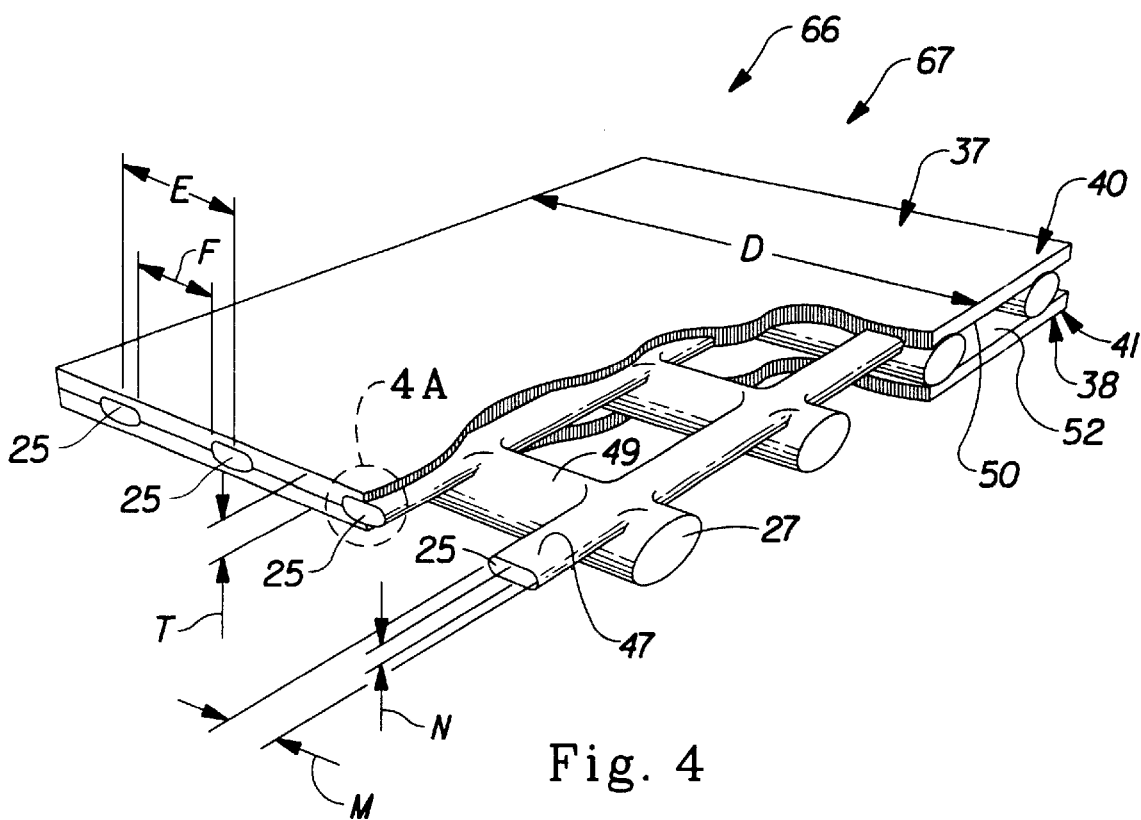
FIG. 4 is a partial perspective view of a laminate structure made in accordance with the present invention, wherein a portion of the carrier layers have been removed to show the integrally bonded first strands.

Referring now to FIGS. 3 and 4 elastic members 36 and 39 comprise a plurality of first strands 24 which intersect or cross (with or without bonding to) a plurality of second strands 26 at nodes 31 at a predetermined angle α, thereby forming a net-like open structure having a plurality of apertures 33. Each aperture 33 is defined by at least two adjacent first strands (i. e., 42 and 43) and at least two adjacent second strands (i. e., 44 and 45) such that apertures 33 are substantially rectangular (preferably square) in shape. Other aperture configurations, such as parallelograms or circular arc segments, can also be provided. Such configurations could be useful for providing non-linear elastic structural directions. It is preferred that first strands 24 are substantially straight and substantially parallel to one another, and, more preferably, that second strands 26 are also substantially straight and substantially parallel to one another. Most preferably, first strands 24 intersect second strands 26 at nodes 31 at a predetermined angle α of about 90 degrees. Each node 31 is an overlaid node, wherein first strands 24 and second strands 26 are preferably joined or bonded (although it is contemplated that joining or bonding may not be required) at the point of intersection with the strands still individually distinguishable at the node. However, it is believed that other node configurations such as merged or a combination of merged and overlaid would be equally suitable.

Although it is preferred that first and second strands 24 and 26 be substantially straight, parallel, and intersect at an angle α of about 90 degrees, it is noted that first and second strands 24 and 26 can intersect at other angles α, and that first strands 24 and/or second strands 26 can be aligned in circular, elliptical or otherwise nonlinear patterns relative to one another. Although for ease of manufacture it is contemplated that first strands 24 and second strands 26 have a substantially circular cross-sectional shape prior to incorporation into laminate structures 66 and/or 67, first and second strands 24 and 26 can also have other cross-sectional shapes such as elliptical, square, triangular, or combinations thereof.

The material of first strands 24 is chosen so that first strands 24 can maintain second strands 26 in relative alignment prior to forming laminate structures 66 and/or 67. It is also desirable that the materials of first and second strands 24 and 26 be capable of being deformed (or initially formed) into predetermined shapes upon application of a predetermined pressure or a pressure in combination with a heat flux, as described in more detail hereafter. These deformed shapes (i. e., elliptical second strands, substantially flat first strands and the like) provide laminate structures 66 and 67 which can be comfortably worn about the body without irritation or other discomfort. It is further desirable that the material chosen for first strands 24 provide an adhesive-like property for joining a portion of second strand outer surface 49 of deformed second strands 27 to a portion of first carrier layer inner surface 50 and second carrier layer inner surface 52.

Figure 4A:
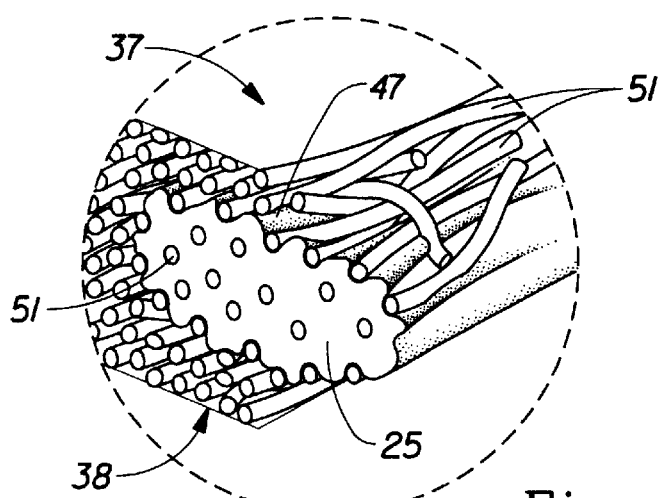
FIG. 4A is an enlarged partial perspective view of an integrally bonded first strand of the laminate structure of FIG. 4.

The material of first strands 24 should also be capable of integrally bonding with carrier layers 37, 38, 40 and/or 41 as part of forming laminate structure 66 and/or 67. As described in more detail hereafter, first strands 24 can be integrally bonded to carrier layers 37, 38, 40 and/or 41 by application of a pressure or a pressure in combination with a heat flux. As used herein, the phrase "integrally bonded" and its derivatives is intended to mean that a portion of a strand outer surface (i. e., first strand outer surface 47) of an integrally bonded strand (i. e., integrally bonded first strands 25) has penetrated into and bonded with carrier layer 37,38, 40, and/or 41. The portion of the strand outer surface of an integrally bonded strand which penetrates carrier layer 37, 38, 40, and/or 41 can bond mechanically (i. e., as by encapsulating, encircling or otherwise engulfing) and/or chemically (i. e., polymerizing, fusing or otherwise chemically reacting) with fibers 51 of carrier layers 37, 38, 40, and/or 41, as shown in FIG. 4A. With regard to penetration, integrally bonded means that a portion of the strand outer surface has penetrated at least about 10%, preferably at least about 25%, more preferably at least about 50%, even more preferably at least about 75%, most preferably about 100% of carrier layer structural thickness T of carrier layer 37, 38, 40, and/or 41 in laminate structure 66 and/or 67. Further, because integrally bonded strands enhance the comfort of laminate structures 66 and/or 67 when worn about the body, at least about 10%, preferably at least about 50%, more preferably at least about 90%, most preferably about 100%, of first strands 24 are integrally bonded to carrier layers 37, 38, 40, and/or 41 of laminate structures 66 and/or 67.

The above described benefits can be achieved by selecting a first strand material having a softening temperature which is lower than the softening temperature of second strands 26 relative to the processing pressures used to form laminate structures 66 and/or 67. As used herein, the phrase "softening temperature" is intended to mean the minimum temperature at which a material begins to flow under an applied pressure to facilitate integral bonding of the material to a carrier layer or layers. Typically, heat is applied to a material to achieve a softening temperature. This generally results in a decrease in the viscosity of the material which may or may not involve a "melting" of the material, the melting being associated with a latent heat of fusion. Thermoplastic materials tend to exhibit a lowering in viscosity as a result of an increase in temperature allowing them to flow when subjected to an applied pressure. It will be understood that as the applied pressure increases, the softening temperature of a material decreases and therefore a given material can have a plurality of softening temperatures because the temperature will vary with the applied pressure. For ease of manufacturing and processing, and when utilizing generally polymeric materials for strands 24 and 26, it is preferred that the softening temperature of first strands 24 be lower, at least about 10° C. lower, more preferably at least about 20° C. lower, than the softening temperature of second strands 26 when both materials are subjected to the same applied pressure (e.g., the processing pressure). As used herein, the phrase "bonding pressure", is intended to mean the pressure which facilitates the integral bonding of first strands 24 to carrier layers 37 and 38, without integrally bonding second strands 26 to carrier layers 37 and 38, when both strands are at the softening temperature of first strands 24 but below the softening temperature of second strands 26. In addition to the selection of first and second strand materials for softening temperature point, second strands 26 are preferably formed from a material which renders second strands 26 appropriately elastic such that laminate structures 66 and/or 67 provide a structural direction, along the direction of second strands 26, which is also appropriately elastic as desired.

Polymers such as polyolefins, polyamides, polyesters, and rubbers (i. e., styrene butadiene rubber, polybutadiene rubber, polychloroprene rubber, nitrile rubber and the like) have been found to be suitable, but not limited to, materials for forming the first and second strands of elastic member 36 and/or 39. Other materials or compounds (i. e., adhesive first strands) having different relative softening temperatures or elasticity can be substituted so long as the material provides the previously described benefits. Additionally, adjunct materials can be added to the base materials comprising first and second strands (i. e., mixtures of pigments, dyes, brighteners, heavy waxes and the like) to provide other desirable visual, structural or functional characteristics.

Elastic members 36 and/or 39 may be formed from one of a variety of processes known in the art. A particularly suitable material for use as first and/or second elastic member 36 and/or 39 is an elastic scrim available as T50018 from Conwed Plastics, Minneapolis, Minn.

Alternatively, first and second elastic members 36 and 39 may each be selected from natural or synthetic rubber, or any number of polymeric materials which are capable of elongation and recovery. Suitable materials include, but are not limited to, styrene block copolymers, rubber, Lycra™, Krayton™, polyethylene including metallocene catalyst PE, foams including polyurethane and polyesters, and the like. First and second elastic members 36 and 39 may be in the form of films, strands, scrims, ribbons, tapes, structural elastic-like film, and the like.

For ease of manufacture and cost efficiency, carrier layers 37, 38, 40, and/or 41 are preferably formed from, but not limited to, a non-woven fabric having fibers formed, for example, from polyethylene, polypropylene, polyethylene terepthalate, nylon, rayon, cotton or wool. These fibers can be joined together by adhesives, thermal bonding, needling/felting, or other methods known in the art to form carrier layers 37, 38, 40 and/or 41. Although it is preferred that carrier layers 37, 38, 40, and/or 41 are formed from a non-woven fabric, other fabrics such as wovens and knits, would be suitable.

The softening temperature of carrier layers 37, 38, 40, and/or 41 (at the subject processing pressures) should be greater than any of the processing temperatures applied to elastic member 36 and/or 39 in forming laminate structures 66 and/or 67. In addition, carrier layers 37, 38, 40, and/or 41 of the present invention preferably have a modulus of less than about 100 gm force per cm at a unit strain $\epsilon_\mu$ of at least about 1 (i. e., $L_f=2 \times L_o$) in a direction along second strands 26 when it is formed into laminate structure 66 and/or 67. As used herein, the term "modulus" is intended to mean the ratio of an applied stress σ to the resulting unit strain $\epsilon_\mu$, wherein stress σ and strain $\epsilon_\mu$ are:

$$\sigma = F_a/W$$

$$\epsilon_\mu = (L_f - L_o)/L_o$$

Where $F_a$=Applied force

W=Orthogonal dimension of the element or structure subjected too the applied force $F_a$ (typically the structure width)

$L_f$=Elongated length $L_o$=Original length

For example, a 20 gram force applied orthogonally across a 5 cm wide fabric would have a stress σ of 4 grams force per cm. Further, if the original length $L_o$ in the same direction as the applied force $F_a$ were 4 cm and the resulting elongated length $L_f$ were 12 cm, the resulting unit strain $\epsilon_\mu$ would be 2 and the modulus would be 2 grams force per cm.

It is believed that a carrier layer having a modulus of less than about 100 grams force per cm in a subject fabric direction will, when the subject fabric direction is juxtaposed co-directional with elastic second strands 26 in laminate structures 66 and/or 67, provide a laminate structure 66 and/or 67 with a modulus along the direction of second strands 26 that is largely a function of the material properties, size, and arrangement of second strands 26. In other words, the modulus of carrier layers 37, 38, 40, and/or 41 will be low enough that the modulus of the second strands 26 will largely determine the modulus of laminate structures 66 and/or 67 in the subject direction. This configuration is especially useful if it is desired that laminate structure 66 and/or 67 provide an elastic structural direction along the direction of deformed laminate second strands 27.

If carrier layers 37, 38, 40 and/or 41 do not inherently provide the desired modulus, carrier layers 37, 38, 40 and/or 41 can be subjected to an activation process before or after forming laminate structures 66 and/or 67. As taught for instance in U.S. Pat. No. 4,834,741, issued to Sabee on May 30, 1989, incorporated in its entirety herein by reference, subjecting carrier layers 37, 38, 40 and/or 41 to an activation process (either separately or as part of laminate structures 66 and/or 67) will plastically deform carrier layers 37, 38, 40 and/or 41 such that it will provide the desired modulus. In an activation process, such as that taught by Sabee, carrier layer 37, 38, 40 and/or 41 (or laminate structure 66 and/or 67 incorporating same) is passed between corrugated rolls to impart extensibility thereto by laterally stretching carrier layers 37, 38, 40 and/or 41 in the cross-machine direction. Carrier layers 37, 38, 40 and/or 41 are incrementally stretched and drawn to impart a permanent elongation and fabric fiber orientation in the cross-machine direction. This process can be used to stretch carrier layers 37, 38, 40 and/or 41 before or after joinder of laminate structures 66 and/or 67. This preferably provides a laminate structure which can be extended in an elastic structural direction with minimal force as carrier layers 37, 38, 40 and/or 41 (and any additional layers) have initially been "activated" or separated in this direction, thereby providing a low modulus in the subject direction such that the laminate structure modulus is primarily a function of laminate second strands 27.

Laminate structures 66 and/or 67 are preferably formed by juxtaposing carrier layers 37, 38, 40 and/or 41 and elastic members 36 and/or 39 and applying a predetermined pressure or a predetermined pressure and heat flux, depending upon the selected materials for carrier layers 37, 38, 40 and/or 41 and elastic members 36 and/or 39, so that first strands 24 are integrally bonded to carrier layers 37, 38, 40 and/or 41. In addition to integrally bonding first strands 24 to carrier layers 37, 38, 49 and/or 41, it is desirable that the above described process deform first strands 24 so that the shape of integrally bonded first strand outer surface 47 is substantially flat. The phrase "substantially flat" and its derivatives, as used herein, means that integrally bonded first strands 25 have a major dimension M (i. e., the largest dimension parallel to the major axis of the strand cross section as shown in FIG. 4) at least about 2 times the length of a minor dimension N (i. e., the smallest dimension parallel to the minor axis of the strand cross section as shown in FIG. 4) Thus, it should be clear that an integrally bonded first strand 25 can have irregularities in outer surface 47 (i. e., peaks and valleys and the like, as shown in FIG. 4A) and still be within the intended meaning of substantially flat. More preferably, it is desirable that a portion of outer surface 47 of integrally bonded first strands 25 is also substantially coplanar with carrier layer inner surfaces 50 and 52 such that minor dimension N is about equal to or less than structural thickness T of carrier layers 37, 38, 40 and/or 41 and substantially all of minor dimension N is located within structural thickness T, as generally shown in FIG. 4. It is further contemplated that variations in the substantially flat and coplanar shapes of integrally bonded first strands 25 can occur along the length of first strands 25 without deviating from the scope of these definitions. In other words, due to processing variations, it is noted that portions of integrally bonded first strands 25 can be substantially flat and/or coplanar while other portions along the same strand may not. These configurations are still considered to be within the definitions of substantially flat and coplanar as set forth above.

The above described shapes of integrally bonded first strands 25 advantageously provide laminate structures 66 and/or 67, wherein strands 25 do not protrude in a manner which would cause irritation or other discomfort when laminate structures 66 and/or 67 are cut (thereby exposing the ends of integrally bonded first strands 25) and worn about the body. As such, at least about 25%, preferably at least about 50%, more preferably at least about 75%, and most preferably about 100% of integrally bonded first strands 25 are substantially flat and coplanar.

In contrast to the substantially flat and coplanar shape of integrally bonded first strands 25 of laminate structures 66 and/or 67, laminate second strands 27 are preferably only joined (as opposed to integrally bonded) to carrier layer inner surfaces 50 and 52, as shown in FIG. 4, by application of the above described pressure and heat flux. It is contemplated, however, that second strands 26 can also be integrally bonded to carrier layers 37, 38, 40 and/or 41 if so desired. The integral bonding of first strands 24 to carrier layers 37, 38, 40 and/or 41 can also be performed such that first strands 24 act as an adhesive to intermittently join second strands 26 to carrier layer inner surfaces 50 and 52 at nodes 31. Alternatively, second strands 26 can comprise a self-adhering material which aids in joining a portion of second strand outer surfaces 49 to carrier layer inner surfaces 50 and 52.

Figure 5:
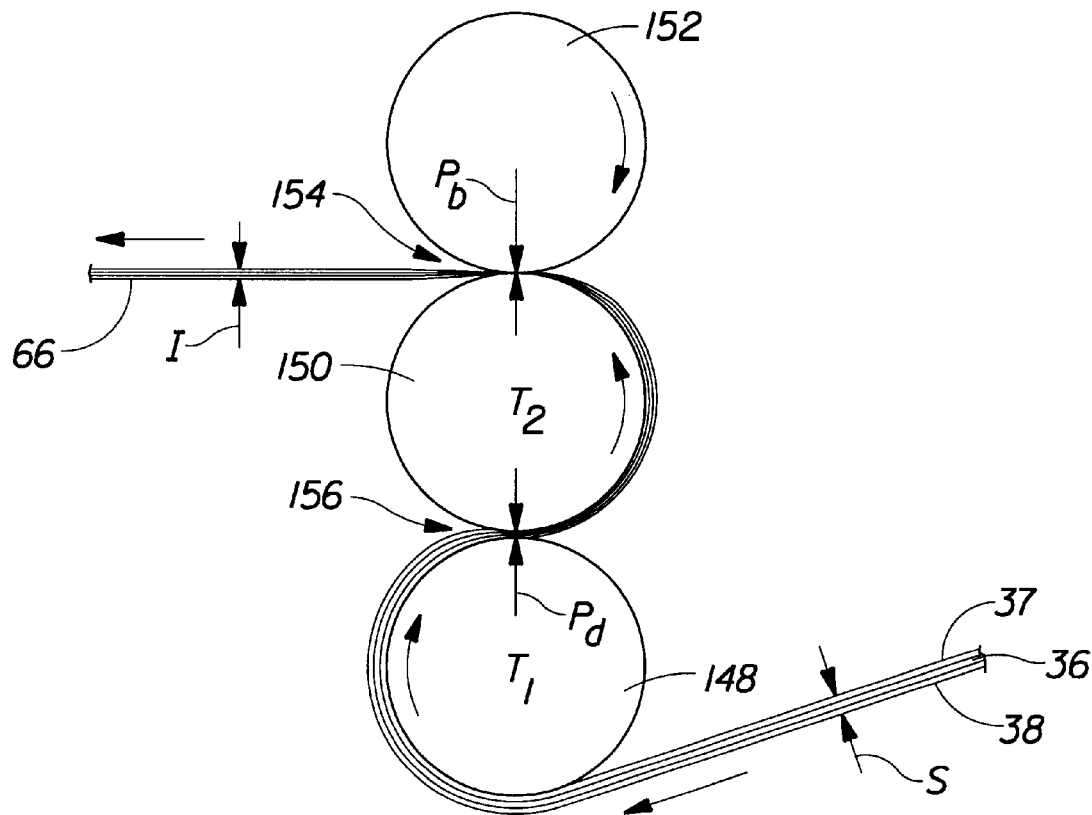
FIG. 5 is a schematic representation of a preferred process according to the present invention for forming the laminate structure of FIG. 4.

As seen in FIG. 5, laminate structures 66 and/or 67 are preferably manufactured by a process comprising a substantially non-resilient first surface 148 (i. e., formed from steel or the like), a substantially non-resilient second surface 150, and a substantially resilient third surface 152 (i. e., formed from a silicone or other deformable rubber), wherein these surfaces are provided in the form of rollers. First surface 148 is spaced adjacent second surface 150 such that gap 156 is formed therebetween, while second surface 150 and third surface 152 are positioned in surface contact to one another thereby forming interference nip 154. Gap 156 is preferably sized such that first strands 24 and second strands 26 pass easily therethrough. Alternatively, gap 156 may be sized such that second strands 26 are deformed by passing therethrough.

First carrier layer 37 is juxtaposed adjacent to first elastic member 36 which is juxtaposed adjacent to second carrier layer 38 such that when fed around first surface 148, as seen in FIG. 5, first elastic member 36 is disposed between first carrier layer 37 and second carrier layer 38. Preferably, first strands 24 of first elastic member 36 are juxtaposed adjacent inner surface 50 of first carrier layer 37 and second strands 26 are juxtaposed adjacent inner surface 52 of second carrier layer 38. First carrier layer 37 is preferably oriented adjacent first surface 148. First surface 148 is heated to a temperature $T_1$, which, in combination with the feed rate of juxtaposed first carrier layer 37, first elastic member 36, and second carrier layer 38 over first surface 148, raises the temperature of first strands 24 to, or above, their softening temperature. Because of the low applied pressure $P_d$ at gap 156, first strands 24 and second strands 26 undergo little if any deformation thereat.

After juxtaposed first carrier layer 37, first elastic member 36, and second carrier layer 38 pass through gap 156, second carrier layer 38 is preferably oriented adjacent second surface 150 and disposed between second surface 150 and first elastic member 36 and first carrier layer 37. Second surface 150 is preferably heated to a temperature $T_2$, which in combination with the feed rate of juxtaposed first carrier layer 37, first elastic member 36, and second carrier layer 38 over second surface 150, raises the temperature of second strands 26 to their softening temperature. Juxtaposed first carrier layer 37, first elastic member 36, and second carrier layer 38 then pass through interference nip 154, wherein first strands 24 are integrally bonded to first carrier layer 37 and second carrier layer 38 by the application of first strand bonding pressure $P_b$ from second and third surfaces 150 and 152 at nip 154. Resilient third surface 152 provides bonding pressure $P_b$ which is uniformly applied to first strands 24 between second strands 26 due to the conforming nature of resilient third surface 152. More preferably, the application of pressure $P_b$ from third surface 152 and heat flux from second surface 150 at temperature $T_2$ is sufficient to deform first strands 24 into substantially flat shaped and integrally bonded first strands 25. Most preferably, the application of pressure and heat flux is sufficient to deform first strands 24 into integrally bonded first strands 25 which are substantially coplanar with inner surface 50 of first carrier layer 37 and second carrier layer 38.

In contrast, at least about 25%, preferably at least about 50%, more preferably at least about 75%, most preferably about 100%, of second strands 26 are deformed into a substantially elliptical shape at nip 154 because pressure $P_b$ is fully applied to second strands 26 by second surface 150. The elliptical cross-sectional shape of second strands 27 is desirable if the undeformed cross section of the second strands 26 would otherwise produce a "nubby" or rough feel when laminate structures 66 and/or 67 are worn about the body. Preferably, the post-nip structural thickness I of laminate structures 66 and/or 67 is about 50% of the pre-nip structural thickness S of juxtaposed first carrier layer 37, first elastic member 36, and second carrier layer 38.

The feed rate of juxtaposed first carrier layer 37, first elastic member 36, and second carrier layer 38 through first, second, and third surfaces 148, 150, and 152 can be adjusted so that first and second strands 24 and 26 have a sufficient residence time adjacent heated first and second surfaces 148 and 150 so that these strands can be softened and deformed as described herein.

Based upon the foregoing described nip process, it has been found that the following will form satisfactory laminate structures 66 and/or 67 having an elastic structural direction along the direction of laminate second strands 27: first, second, third, and fourth carrier layers 37, 38, 40 and 41 preferably comprise a carded nonwoven formed from thermally bonded polypropylene and having a 32 gram per m$^2$ basis weight, a fiber size of about 2.2 denier per filament, a caliper of between about 0.01 cm to about 0.03 cm, a modulus of about 100 grams force per cm at a unit strain $\epsilon_\mu$ of 1 (such a fabric being marketed by Fibertech, Landisville, N.J., as Phobic Q-1); and first and second elastic members 36 and 39 comprise a mesh wherein first strands 24 are formed from polyethylene and second strands 26 are formed from a styrene or butadiene block copolymer (such a mesh being manufactured by Conwed, Minneapolis, Minn. and marketed as T50018). Specifically, the juxtaposed Phobic Q-1 fabric, T50018 mesh, and Phobic Q-1 fabric, having a pre-formed structural thickness S of from about 0.09 cm to about 0.13 cm, preferably from about 0.10 cm to about 0.12 cm, more preferably about 0.11 cm, are fed at a rate of from about 6 to about 14, more preferably from about 7 to about 12, most preferably from about 8 to about 10 meters per minute, over first surface 148 which is heated to a temperature $T_1$ of from about 71° C. to about 141° C., preferably from about 130° C. to about 141° C., more preferably from about 137° C. to about 139° C. In a preferred arrangement, gap 156 is preferably greater than or about 0.13 cm. Preferably, second surface 150 is heated to a temperature $T_2$ of from about 71° C. to about 141° C., preferably from about 130° C. to about 141° C., more preferably from about 137° C. to about 139° C., as the juxtaposed fabrics and mesh pass over second surface 150 and through inference nip 154. Pressure $P_b$ at nip 154 is preferably from about 55 to about 85 kilograms per centimeter, more preferably from about 70 to about 75 kilograms per centimeter. After the juxtaposed fabrics and mesh emerge from nip 154, the resulting thermal bonded elastic laminates 66 and/or 67 have a thickness I of from about 0.05 cm to about 0.09 cm, preferably from about 0.06 cm to about 0.08 cm, more preferably about 0.07 cm.

Figure 6:
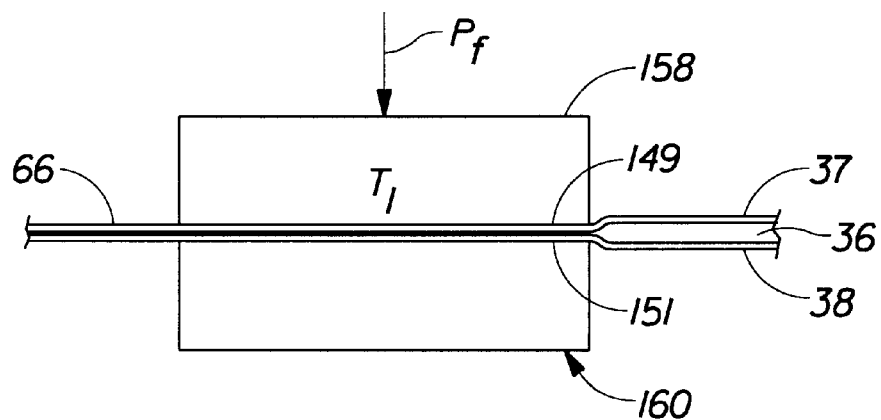
FIG. 6 is a schematic representation of a plate process according to the present invention for forming the laminate structure of FIG. 4.

In addition to forming a laminate structure of the present invention via the is above described nip process, such laminate structures can also be formed by a process providing a first plate 150 and a second plate 160, such as shown in FIG. 6. In contrast to the process discussed previously, first plate surface 149 preferably is substantially non-resilient, while second plate surface 151 is substantially resilient. First plate surface 149 is preferably heated to temperature $T_1$. A bonding pressure $P_f$ is applied to the juxtaposed fabrics and mesh by moving first plate surface 149 toward second plate surface 151 appropriately. Because temperature $T_1$ heats first strands 24 to their softening temperature for the applied bonding pressure $P_f$, application of the bonding pressure $P_f$ integrally bonds first strands 24 to carrier layers 37 and 38. More preferably, application of the bonding pressure $P_f$ also deforms first strands 24 into a substantially flat shape which is also coplanar with carrier layer inner surfaces 50 and 52. Most preferably, application of bonding pressure $P_f$ also deforms second strands 26 into a substantially elliptical shape.

Using the Phobic Q-1 fabrics and T50018 mesh combination described above, satisfactory laminate structures 66 and/or 67 having first strands 24 integrally bonded to first and second carrier layers 37 and 38 can be provided if first plate 158 is heated to a temperature $T_1$ of from about 110° C. to about 130° C. and a bonding pressure $P_f$ of between 350 to 700 grams force per cm² is applied between first plate 158 and second plate 160 for from about 10 to about 20 seconds.

While the above description describes the process for making first thermal bonded elastic laminate 66 (i.e., comprising first carrier layer 37, first elastic member 36, and second carrier layer 38), an identical process for making second thermal bonded elastic laminate 67 (i.e., comprising third carrier layer 40, second elastic member 39, and fourth carrier layer 41) may be utilized.

It is believed that properly selecting the strand density, strand cross-sectional area, and/or the melt index of first strands 24 (if first strands 24 are formed of a polymer) is necessary in order to provide laminate structures 66 and/or 67 having an elastic structural direction along the direction of the second strands 27. Improper selection of strand density, strand cross-sectional area, and/or melt index of first strands 24 can result in a laminate structure wherein portions of integrally bonded first strands 25 can overlap or merge together in laminate structures 66 and/or 67. Such merging or overlap of integrally bonded first strands 25 can result in only small portions of laminate second strands 27 being able to extend or elongate when subjected to a tensile force, as opposed to the elongation being distributed along substantially the entire length of substantially all of laminate second strands 27 absent this overlap. To minimize this condition, the strand density, strand cross-sectional area, and/or melt index of first strands 24 should be selected such that integrally bonded first strands 25 have a strand coverage $S_c$ of less than about 50%. As used herein, the phrase "strand coverage" is intended to be a measure of the amount of surface area of first carrier layer inner surface 50 and second carrier layer inner surface 52 which is in contact with integrally bonded first strands 25 of the present invention. Strand coverage Sc is defined as:

$$S_c = (E-F)/E * 100$$

Where
E=strand centerline distance between any adjacent integrally bonded first strands 25, as shown in FIG. 4

F=strand edge distance F between any adjacent integrally bonded first strands 25, as shown in FIG. 4

The measurements of E and F can be taken at any cross section through laminate structure 66 and/or 67 between any adjacent integrally bonded first strands The phrase "strand density", as used herein, is intended to mean the number of subject strands per centimeter along a strand transverse to the subject strands. For example, first strands 24 have a strand density which can be measured over a predetermined length A of a second strand 26, as shown in FIG. 3. Likewise, second strands 26 have a strand density which can be measured over a predetermined length B of a first strand 24. The phrase "strand cross-sectional area", as used herein, is intended to mean the cross-sectional area of any first strand 24 when measured according to techniques known in the art.

The melt index of a polymer measures the ability of the polymer to flow when subjected to a given temperature or pressure. A polymer having a low melt index will be more viscous (and therefore not flow as readily) at a given temperature than a polymer having a higher melt index. Thus, it is believed that first strands 24 comprising a polymer having a high melt index will have a greater tendency to merge or overlap during application of a given pressure and heat flux than first strands 24 comprising a polymer having a lower melt index and subjected to the same pressure and heat flux. Because of this variability, the polymer forming first strands 24 can be selectively chosen, in conjunction with the strand density and strand cross-sectional area, to provide a predetermined melt index such that first strands 24 are integrally bonded to first and second carrier layer 37 and 38 with a strand coverage $S_c$ of about 50 percent. In addition, varying the polymer melt index can also be especially useful where it is desired to increase the density of first and second carrier layers 37 and 38 while maintaining the same processing conditions. In this situation, the polymer of first strands 24 can be changed to provide a higher melt index such that first strands 24 can more easily penetrate and bond with carrier layer 37, 38, 40, and/or 41 when subjected to the predetermined pressure and heat flux. Consequently, the same level of integral bonding can be achieved without changing the processing conditions despite the increased density of carrier layers 37, 38, 40, and/or 41.

Based upon the foregoing, it is believed that first strands 24 should preferably be aligned so as to provide a strand density of from about 2 to about 10 strands per centimeter in conjunction with a strand cross-sectional area of from about 0.0005 cm² to about 0.03 cm², more preferably from about 3 to about 6 strands per centimeter in conjunction with a strand cross-sectional area of from about 0.001 cm² to about 0.005 cm², so that merger or overlap of integrally bonded first strands 25 in laminate structure 66 and/or 67 can be avoided. A melt index of from about 2 to about 15 (as measured per ASTM D1238) in conjunction with the above-described strand density and strand cross-sectional area values has been found to be satisfactory. With regard to second strands 26, it is believed that the strand density, strand cross-sectional area, and modulus of second strands 26 can also affect the elastic properties of laminate structures 66 and/or 67 (i. e., the modulus of laminate structures 66 and/or 67) in the direction along the second strands 26 (i. e., along irection D of FIG. 4). For example, as the strand density and/or the strand cross-sectional area of second strands 26 increases, the modulus of laminate structures 66 and/or 67 will decrease. For laminate structures 66 and/or 67 to be incorporated into the wraps of the present invention, it is desirable that a modulus of from about 100 to about 250 grams force per cm, at a strain $\epsilon_u$ of about 1 be provided. It is believed that providing second strands 26 having a strand density of from about 2 to about 5, a cross-sectional area of from about 0.003 cm$^2$ to about 0.02 cm$^2$, and comprising a styrene butadiene block copolymer will provide laminate structures 66 and/or 67 having the preferred modulus in a direction along second strands 26. The modulus of laminate structures 66 and/or 67 can be measured by techniques known in the art. For example, the modulus of laminate structures 66 and/or 67 can be measured using a universal constant rate of elongation tensile tester, such as Instron Model #1122, manufactured by Instron Engineering Corp., Canton, Mass.

Laminate structures 66 and/or 67 can also be subjected to various additional post-formation processes known in the art. For example, a laminate structure made in accordance herewith can comprise additional fabric layers (i.e., bulking layers) which are joined to the laminate structure so as to further improve the wearability and comfort of the structure. The additional fabric layers can be secured to the laminate structure by adhesive, thermal bonding, pressure bonding, ultrasonic bonding, dynamic mechanical bonding, or any other suitable methods known in the art.

To improve the elastic performance of wrap 10, elastic portion 20 may be subjected to an activation process after assembly and prior to use. This activation process stretches and permanently deforms on a very small scale the nonelastic layers of wrap 10. This activation process allows first and/or second thermal bonded elastic laminate 66 and/or 67 to stretch or expand in the direction of an applied force and essentially return to their original dimensions upon removal of the force, unencumbered by the nonelastic layers of elastic portion 20.

Alternatively, elastic portion 20 may be assembled while first and/or second thermal bonded elastic laminates 66 and/or 67 are held in an extended state. After assembly, the first and/or second thermal bonded elastic laminates 66 and/or 67 are allowed to return to their relaxed state causing the nonelastic layers of elastic portion 20 to fold and buckle creating rugosities. Subsequent stretching of elastic portion 20 will result in the unfolding of these rugosities.

In a preferred embodiment of the present invention there is a second elastic portion 56 located intermediate heat cells 75 and/or thermal packs 22. Materials and processes used to deliver elastic portion 20 described herein above may also be used to deliver second elastic portion 56.

A particular embodiment of wrap 10 is described which has two thermal bonded elastic laminates 66 and 67, which are coextensive body-facing material 62 and outer surface material 64. Preferably, first and second thermal bonded elastic laminates 66 and 67 extend from first end 14 to second end 16 of flexible material 12. Alternatively, first and second thermal bonded elastic laminates 66 and 67 may extend from first end 14 to interfacial centerline 54 of flexible material 12 to provide elastic properties to first and second straps 80 and 82. Interfacial centerline 54 is preferably aligned perpendicular to longitudinal axis 18 located between first end 14 and second end 16.

A particular embodiment of wrap 10 is described which utilizes a number of layers. Alternatively, wrap 10 could be comprised of a single elastic member. First carrier layer 37 and second carrier layer 38 are employed during the thermal bonding of first elastic member 36 and third carrier layer 40 and fourth carrier layer 41 are employed during the thermal bonding of second elastic member 39. If the thermal bonding step is not used for any number of reasons, then first carrier layer 37, second carrier layer 38, third layer 40, and fourth carrier layer 41, may be omitted.

Body-facing material 62 of flexible material 12 comprises body-facing surface 28 coextensive from first end 14 to second end 16. Body-facing material 62 comprises a plurality of loop elements 102 which are formed from fibers of material 62. Similarly, outer surface material 64 of flexible material 12 comprises outer surface 30 coextensive from first end 14 to second end 16. Outer facing material 64 comprises a plurality of loop elements 104 which are formed from fibers of material 64. The plurality of loop elements 102 and 104 serve as one-half of a reclosable hook and loop fastening system. As used herein, the term "reclosable", refers to that property of a fastening system which provides for initial closing of the fastening system, a subsequent opening of the fastening system, followed by at least one additional closings of the same fastening system. The subsequent closing of the fastening system may either return the closure to the original position or it may result in a repositioning of the closure from the initial configuration.

Body-facing surface 28 comprises at least one hook member 34 which is permanently attached to body-facing surface 28 near first end 14. Similarly, outer surface 30 comprises at least one hook member 32 which is permanently attached to outer surface 30 near second end 16. The plurality of hooks on hook members 32 and 34 serves as the second half of a reclosable hook and loop fastening system. As used herein, the term "permanently attached", is defined as the joining of two or more elements which remain joined during their intended use.

Hook member 32 with loop elements 102 and hook member 34 with loop elements 104, provide a reclosable hook and loop fastening system for securing wrap 10 around the user's knee or elbow.

Alternatively, the reclosable fastening system of wrap 10 may be a single hook and loop fastening system comprising either hook member 32 and loop elements 102 or hook member 34 and loop elements 104.

Body-facing material 62 and outer surface material 64 may be any number of different materials which include, but are not limited to, woven and knit fabrics, carded nonwovens, spunbond nonwovens, and the like. A material that has been found to be particularly suitable for body-facing material 62 and outer surface material 64 is a carded thermally bonded nonwoven of polypropylene with a basis weight of 32 grams per square meter (gsm). This material is available as grade #9327786, from Veratec, Walpole, Mass.

The hooks of hook members 32 and 34 may be any number of styles, shapes, and/or densities depending upon the use. The hooks of hook members 32 and 34 may be bent shafts, mushroom capped, harpoon-shaped, or any other suitable shape, unidirectional, bi-directional, or omni-directional, depending upon the application and companion loop elements of loop members 102 and 104. The hooks of hook members 32 and 34 must be chosen in conjunction with companion loop elements of loop members 102 and 104 so as to provide the peel and shear forces that are required for different applications.

The attachment of layers to form body-facing laminate 92, outer surface laminate 93 and, finally, wrap 10 may be achieved by any number of attachment means known in the art. These include, but are not limited to, hot melt adhesive including spiral sprays, meltblown, control coat, and the like, latex adhesives applied via spray, printing gravure, and the like, thermal bonding, ultrasonic, pressure bonding, and the like. One particular method that has been used successfully is hot melt adhesive layer 60 available as 70-4589 from National Starch and Chemical Co., Bridgewater, N.J., applied via a spiral hot melt system at a rate of from about 0.5 to about 25 mg/cm$^2$.

Flexible material 12 preferably comprises first strap portion 80 and second strap portion 82, each having at least one hook member 34 which can be independently fastened to loop members 104. Upon application of wrap 10, first end 14 of upper strap portion 80 encircles behind the user's knee or in front of the user's elbow, preferably above the knee or elbow, and first end 14 of second strap portion 82 encircles behind the user's knee or in front of the user's elbow, preferably below the knee or elbow. First end 14 of first and second strap portions 80 and 82 overlap second end 16 such that, hook members 32 on outer surface 30 near second end 16 engage loop elements 102 on body-facing surface 28. Engagement of hook members 32 with loop elements 102 forms the first part of the two-part hook and loop fastening system. Continuing the application, hook members 34 on the body-facing surface 28 near first end 14 are placed in contact with loop elements 104 of outer surface 30 forming the second part of a two-part hook and loop fastening system. First strap portion 80 and second-strap portion 82 allow easier application and differential tensioning of material 12 during use. Additional strap portions may optionally be included.

Preferably, first and second strap portions 80 and 82 contain elastic portion 20 of flexible material 12. That is first and second strap portions 80 and 82 preferably exhibit elastic behavior when stretched in a direction parallel to longitudinal axis 18.

Flexible material 12 preferably comprises a body portion 81. Body portion 81 has a first edge 83 and a second edge 84. The distance between first edge 83 and second edge 84 measured in a direction transverse longitudinal axis 18 is the width of body portion 81 of flexible material 12. First strap portion 80 of flexible material 12 has a first edge 85 and a second edge 86. The distance between first edge 85 and second edge 86 measured in a direction transverse longitudinal axis 18 is the width of first strap portion 80 of flexible material 12. Second strap portion 82 of flexible material 12 has a first edge 87 and a second edge 88. The distance between first edge 87 and second edge 88 measured in a direction transverse longitudinal axis 18 is the width of second strap portion 82 of flexible material 12.

Flexible material 12 preferably comprises an aperture 46 between interfacial centerline 54 and second end 16. Aperture 46 is intended to be aligned with the wearer's patella or olecranon and serves to help properly position wrap 10 during use. Preferably, flexible material 12 has at least one slit 48, more preferably two slits, extending from aperture 46, one toward second end 16 and the other toward interfacial centerline 54. Slit(s) 48 allows flexible material 12 to expand and close respectively as the user bends and straightens his/her knee or elbow. Slit(s) 48 may be of any shape, however, the rectangular shape, as depicted in FIG. 1, is preferred. In the alternative, flexible material 12 may comprise slit 48 without aperture 46.

Wrap 10 may further comprise stays 100. Stays 100 are preferably embedded transverse to the longitudinal axis 18 and internally in the layers of flexible material 12 of wrap 10 and positioned adjacent interfacial centerline 54 and/or second end 16 of flexible material 12. Stays 100 are preferably stripes of glue which are positioned to permit wrap 10 to bend with the knee or elbow, but minimizes bunching of flexible material 12, which would otherwise occur after several knee or elbow bending cycles. Stays 100 serve as resilient stiffeners to cause wrap 10 to maintain its flatness against the user's leg or arm. Alternatively, stays 100 may be positioned on the outer surface 30 of wrap 10. Typically, stays 100 extend to just short of the perimeter edges of wrap 10 so that the stiff ends of stays 100 are never in contact with user's leg or arm. However in a second alternative, the stays 100 may be positioned on body-facing surface 28 to increase friction between wrap 10 and user's leg or arm in order to reduce slippage of wrap 10 during use.

A preferred glue for stays 100 is HL1460-X made by Fuller, Minneapolis, Minn. Beads of about 5 mm in diameter are extruded onto the flexible material 12 with a conventional hot melt glue gun. The glue beads are then calendered or flattened via a compression roll to a thickness of from about 0.3 mm to about 5 mm, which determines the desired stays 100 stiffness.

Alternatively, stays 100 may be made of rigid plastic or metal because these materials may be applied more easily and are less costly to include. With rigid plastic and metal stays, pockets are typically sewn into wrap 10, and then individual stays are formed and installed.

Body-facing surface 28 may optionally comprise foamed polymer strips aligned transverse to longitudinal axis 18 of flexible material 12 for increasing friction between wrap 10 and wearer's knee or elbow. If present, foamed polymer strips are typically located adjacent second end 16 and interfacial line 54. The increased friction provided by foamed polymer strips serves to reduce slippage or relative movement between wrap 10 and the wearer. If present, the foam strips are typically about 25 mm wide and about 1.5 mm thick. High-tack polymers such as ethylene vinyl acetate copolymer (EVA) may be used instead of foamed polymer strips. The polymer strips may also serve as stays 100 and may be glued, thermally bonded or printed onto body-facing surface 28.

Wrap 10 also comprises one or more heat cells 75, preferably arranged in a pattern, as indicated in FIG. 1. Heat cells 75 apply heat energy to the sides and top of the knee or elbow when flexible material 12 is secured around the user's knee or elbow. Heat cells 75 are typically constructed by forming a pocket 76 in base material 70. Pocket 76 in base material 70 is then filled with an exothermic composition 74. After filling pocket 76 in base material 70 with an exothermic composition 74, a cover material 72 is placed over pocket 76 and heat sealed to base material 70 around the periphery of pocket 76, encapsulating exothermic composition 74, thereby forming heat cell 75.

Heat cells 75 are spaced apart from each other and each heat cell 75 functions independently of the rest of the heat cells 75. Each heat cell 75 preferably comprise a densely packed, particulate exothermic composition 74 which preferably substantially fills the available cell volume within the cell reducing any excess void volume thereby minimizing the ability of exothermic composition 74 to shift within the cell. Alternatively, exothermic composition 74 may be compressed into direct compaction articles before being placed into each cell.

Because the heat generating material is densely packed or compressed into direct compaction articles, heat cells 75 is not readily flexible. Therefore, the spacing apart of heat cells 75 and the materials selected for base material 70 and cover material 72 between heat cells 75 allows wrap 10 to easily conform to the user's knee or elbow. Preferably, wrap 10 comprises one or more thermal packs 22 which comprise a plurality of individual heat cells 75, preferably embedded within the laminate structure of the thermal pack 22.

Thermal pack 22 may be made of any number of thermoplastic materials; however, it is preferred that base material 70 and/or cover material 72 be made of thermoplastic materials which are semirigid at a temperature of about 25° C. and below and which soften, i. e., become substantially less rigid, at a temperature above about 25° C. Different materials may be capable of satisfying the specified requirement provided that the thickness is adjusted accordingly. Such materials include, but are not limited to, polyethylene, polypropylene, nylon, polyester, polyvinyl chloride, polyvinylidene chloride, polyurethane, polystyrene, saponified ethylene-vinyl acetate copolymer, ethylene-vinyl acetate copolymer, natural rubber, reclaimed rubber, synthetic rubber, and mixtures thereof. These materials may be used alone or coextruded with a low melt temperature polymer including, but not limited to, ethylene vinyl acetate copolymer, low density polyethylene, and mixtures thereof. Such materials are also capable of containing exothermic composition 74 and limiting oxygen flow into pocket 76 and provides sufficient rigidity to prevent wrap 10 from folding or bunching during use, preventing unacceptable stretching of structures of the continuous layer during processing or use, and deterring easy access to the heat cell contents.

A particular base material 70 and cover material 72, which has proven to be satisfactory, preferably comprises a coextruded film, having a first side of polypropylene and a second side of EVA, and having a combined thickness of from about 20 $\mu$m to about 30 $\mu$m, preferably about 25 $\mu$m. The polypropylene comprises from about 10% to about 90%, preferably from about 40% to about 60%, of the thickness of base material 70 and cover material 72. When coextruded films of the type just described are used for base material 70 and cover material 72, the EVA sides are preferably oriented toward each other to facilitate thermal bonding of cover material 72 to base material 70.

Exothermic composition 74 may comprise any composition capable of providing heat. However, exothermic composition 74 preferably comprises a particulate mix of chemical compounds that undergo an oxidation reaction during use. Exothermic composition 74 may also be formed into agglomerated granules, direct compacted into compaction articles such as granules, pellets, tablets, and/or slugs, and mixtures thereof. The mix of compounds typically comprises iron powder, carbon, a metal salt(s), and water. Mixtures of this type react when exposed to oxygen, providing heat for several hours. Exothermic compositions suitable for inclusion in wrap 10 of the present invention may be found in WO9701313, published Jan. 16, 1997, to Burkett, et al., incorporated in its entirety herein by reference.

Heat cells 75 may comprise any geometric shape, e.g., disk, triangle, pyramid, cone, sphere, square, cube, rectangle, rectangular parallelepiped, cylinder, ellipsoid and the like. The preferred shape of heat cell 75 comprises a disk shaped geometry having a cell diameter of from about 0.2 cm to about 10 cm, preferably from about 0.5 cm to about 8 cm, more preferably from about 1 cm to about 5 cm, and most preferably from about 1.5 cm to about 3 cm. Heat cell 75 may comprise a height of from about 0.08 cm to about 1 cm, preferably from about 0.15 cm to about 0.9 cm, more preferably greater than from about 0.2 cm to about 0.8 cm, and most preferably about 0.4 cm.

The ratio of fill volume to cell volume of heat cell 75 is from about 0.7 to about 1.0, preferably from about 0.75 to about 1.0, more preferably from about 0.8 to about 1.0, even more preferably from about 0.85 to about 1.0, and most preferably from about 0.9 to about 1.0.

Oxygen permeability can be provided by selecting materials for the base material 70 and/or cover material 72 that have the specifically desired permeability properties. The desired permeability properties may be provided by microporous films or by films which have pores or holes formed therein. The formation of these holes/pores may be via extrusion cast/vacuum formation or by hot needle aperturing. Oxygen permeability can also be provided by perforating at least one of the base material 70 and cover material 72 with aeration holes using, for example, an array of pins having tapered points and diameters of from about 0.2 mm to about 2 mm, preferably from about 0.4 mm to about 0.9 mm. Oxygen diffusion into heat cell 75 during oxidation of the exothermic composition 74 typically ranges from about 0.01 cc $O_2$/min./5 $cm^2$ to about 15.0 cc $O_2$/min./5 $cm^2$ (at 21° C., 1 ATM), preferably from about 0.9 cc $O_2$/min./5 $cm^2$ to about 3 cc $O_2$/min./5 $cm^2$ (at 21° C., 1 ATM).

The velocity, duration, and temperature of the thermogenic oxidation reaction of the exothermic composition 74 can be controlled as desired by changing the area of contact with air, more specifically, by changing the oxygen diffusion/permeability.

Elastic thermal uniaxial joint wrap 10 may optionally comprise a layer of material located preferably on body-facing surface 28 of flexible material 12. The layer of material is generally coextensive flexible material 12 from second end 16 to interfacial centerline 54. The layer of material has elasticity in a direction transverse to longitudinal axis 18 of flexible material 12 and preferably, has an elastic recovery force which is as low as possible to minimize forces transverse to longitudinal axis 18. The layer of material is typically attached to body-facing surface 28 along the perimeter of the layer of material using an adhesive. The layer of material provides coverage of the knee or elbow when the user's knee or elbow is bent and flexible material 12 expands separating slit(s) 48. Such a material may comprise a flexible thermal laminate, such as those described herein for first and second thermal layer elastic laminates 66 and 67.

Alternatively the layer of material may have elasticity in a direction parallel to longitudinal axis 18 in addition to elasticity in a direction transverse to longitudinal axis 18.

When assembling wrap 10 for a knee, the width of body portion 81 of flexible material 12 is preferably from about 15 cm to about 25 cm, more preferably from about 18 cm to about 23 cm and most preferably from about 19 cm to about 21 cm. The width of first strap portion 80 and second strap portion 82 of flexible material 12 is typically less than the width of body portion 81 of flexible material 12, preferably from about 2.5 cm to about 13 cm, more preferably from about 4 cm to about 8 cm, and most preferably from about 5 cm to about 7 cm.

When assembling wrap 10 for an elbow, the above described dimensions are preferably scaled appropriately to fit a user's elbow.

Preferably, finished wrap 10 is typically enclosed within a substantially oxygen impermeable package. To use, wrap 10 is removed from the oxygen impermeable package allowing oxygen to enter heat cell 75 and react with exothermic composition 74.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

What is claimed is:

1. A disposable elastic thermal uniaxial joint wrap comprising:
   a) a piece of flexible material having a first end and a second end, a body portion fixed between said first end and said second end, a first strap portion, and a second strap portion, wherein at least one of said body portion, first strap portion, and second strap portion, comprises one or more elastic laminate structures, said laminate structures comprising a first carrier layer, a second carrier layer, and a mesh disposed between said carrier layers, said mesh having a plurality of first strands intersecting a plurality of elastic second strands, said first and second strands having softening temperatures at an applied pressure, at least about 10% of said first strands being integrally bonded to said first carrier layer and said second carrier layer by application of a bonding pressure at said softening temperature of said first strands, wherein at least one of said body portion, first strap portion, and second strap portion is stretchable along a longitudinal axis of said piece of flexible material;
   b) one or more heat cells comprising an exothermic composition spaced apart and fixedly attached across said body portion; and
   c) a fastening means to hold said piece of flexible material around a user's knee or elbow.

2. A disposable elastic thermal uniaxial joint wrap according to claim 1 wherein at least 50% of said first strands are integrally bonded to said first carrier layer and said second carrier layer.

3. A disposable elastic thermal uniaxial joint wrap according to claim 2 wherein at least 90% of said first strands are integrally bonded to said first carrier layer and said second carrier layer.

4. A disposable elastic thermal uniaxial joint wrap according to claim 1 wherein said softening temperatures of said first and second strands are distinct at said bonding pressure, the softening temperature of said first strands being less than the softening temperature of said second strands.

5. A disposable elastic thermal uniaxial joint wrap according to claim 1 wherein said first carrier layer and said second carrier layer each have an outer surface and at least about 50% of said integrally bonded first strands are substantially flat in shape and coplanar with said outer surfaces.

6. A disposable elastic thermal uniaxial joint wrap according to claim 1 wherein at least 25% of said second strands have a substantially elliptical cross-sectional shape.

7. A disposable elastic thermal uniaxial joint wrap according to claim 6 wherein at least 50% of said second strands have a substantially elliptical cross-sectional shape.

8. A disposable elastic thermal uniaxial joint wrap according to claim 7 wherein at least 90% of said second strands have a substantially elliptical cross-sectional shape.

9. A disposable elastic thermal uniaxial joint wrap according to claim 1 wherein said integrally bonded first strands have a strand coverage of less than about 50 percent.

10. A disposable elastic thermal uniaxial joint wrap according to claim 1 wherein said heat cells comprise a densely packed particulate composition comprising iron powder, carbon, a metal salt, and water, said composition substantially fills the available cell volume within said heat cell reducing any excess void volume thereby minimizing the ability of said particulate composition to shift within said heat cells.

11. A disposable elastic thermal uniaxial joint wrap according to claim 10 wherein said heat cells comprise the shape of a disk having a diameter of from about 0.2 cm to about 10 cm and a height of greater than from about 0.2 cm to about 1.0 cm.

12. A disposable elastic thermal uniaxial joint wrap according to claim 11 wherein said heat cells comprise an exothermic composition having a physical form selected from the group consisting of dry agglomerated granules, direct compaction articles, and mixtures thereof, said compaction articles are selected from the group consisting of granules, pellets, tablets, slugs, and mixtures thereof.

13. A disposable elastic thermal uniaxial joint wrap according to claim 1 wherein said strap portions comprise said elastic laminate structures.

14. A disposable elastic thermal uniaxial joint wrap according to claim 1 wherein said body portion further comprises an aperture intended to be aligned with the user's patella or olecranon to establish a convenient locating point for wrapping said wrap around the user's knee or elbow.

15. A disposable elastic thermal uniaxial joint wrap according to claim 14 wherein said body portion further comprises at least one slit extending substantially longitudinally from said aperture for enabling said piece of flexible material to stretch transverse to said longitudinal axis at said aperture in order to accommodate bending of the user's knee or elbow.

16. A disposable elastic thermal uniaxial joint wrap according to claim 1 wherein said body portion further comprises at least one slit extending substantially along the longitudinal axis of said body portion enabling said piece of flexible material to stretch transverse to said longitudinal axis of said body portion in order to accommodate bending of the user's knee or elbow.

17. A disposable elastic thermal uniaxial joint wrap according to claim 1 wherein said flexible material further comprises one or more stays to resiliently stiffen said flexible material and thereby minimize bunching of said flexible material when said user's knee or elbow is repeatedly bent.

18. A disposable elastic thermal uniaxial joint wrap according to claim 1 wherein said fastening system is reclosable.

19. A disposable elastic thermal knee wrap according to claim 18 wherein said reclosable fastening system comprises a hook and loop fastening system.

20. A disposable elastic thermal uniaxial joint wrap according to claim 19 wherein said reclosable fastening system comprises a two part hook and loop fastening system.

21. A disposable elastic thermal uniaxial joint wrap comprising:
   a) a piece of flexible material having a first end and a second end, a body portion fixed between said first end and said second end, a first strap portion, and a second strap portion, wherein at least one of said body portion, first strap portion, and second strap portion, comprises one or more elastic laminate structures, said laminate structures comprising a first carrier layer, a second carrier layer, and a mesh disposed between said carrier layers, said mesh having a plurality of first strands intersecting a plurality of elastic second strands, said first and second strands having softening temperatures at an applied pressure, at least about 10% of said first strands being integrally bonded to said first carrier layer and said second carrier layer by application of a bonding pressure at said softening temperature of said first strands, wherein at least one of said body portion, first strap portion, and second strap portion is stretchable along a longitudinal axis of said piece of flexible material;

b) one or more thermal packs fixedly attached to said body portion, each thermal pack having a unified structure comprising at least one continuous layer of material and a plurality of individual heat cells spaced apart and fixedly attached to said continuous layer of material; and c) a fastening means to hold said piece of flexible material around a user's knee or elbow.

22. A disposable elastic thermal uniaxial joint wrap according to claim 21 wherein said softening temperatures of said first and second strands are distinct at said bonding pressure, the softening temperature of said first strands being less than the softening temperature of said second strands.

23. A disposable elastic thermal uniaxial joint wrap according to claim 21 wherein said first carrier layer and said second carrier layer each have an outer surface and at least about 50% of said integrally bonded first strands are substantially flat in shape and coplanar with said outer surfaces.

24. A disposable elastic thermal uniaxial joint wrap according to claim 21 wherein at least 25% of said second strands have a substantially elliptical cross-sectional shape.

25. A disposable elastic thermal uniaxial joint wrap according to claim 21 wherein said integrally bonded first strands have a strand coverage of less than about 50 percent.

26. A disposable elastic thermal uniaxial joint wrap according to claim 21 wherein said thermal pack comprises at least one continuous layer of a coextruded material having a first side of polypropylene and a second side of a low melt temperature copolymer, wherein said continuous layer is semirigid at a temperature of about 25° C. and below, and substantially less rigid at a temperature of above about 25° C.

27. A disposable elastic thermal uniaxial joint wrap according to claim 21 wherein said heat cells comprise a densely packed particulate composition comprising iron powder, carbon, a metal salt, and water, said composition substantially fills the available cell volume within said heat cell reducing any excess void volume thereby minimizing the ability of said particulate composition to shift within said heat cells.

28. A disposable elastic thermal uniaxial joint wrap according to claim 21 wherein said heat cells comprise an exothermic composition having a physical form selected from the group consisting of dry agglomerated granules, direct compaction articles, and mixtures thereof, said compaction articles are selected from the group consisting of granules, pellets, tablets, slugs, and mixtures thereof.

29. A disposable elastic thermal uniaxial joint wrap according to claim 21 wherein said strap portions comprise said elastic laminate structures.

30. A disposable elastic thermal uniaxial joint wrap according to claim 21 wherein said body portion further comprises an aperture intended to be aligned with the user's patella or olecranon to establish a convenient locating point for wrapping said wrap around the user's knee or elbow.

31. A disposable elastic thermal uniaxial joint wrap according to claim 30 wherein said body portion further comprises at least one slit extending substantially longitudinally from said aperture for enabling said piece of flexible material to stretch transverse to said longitudinal axis at said aperture in order to accommodate bending of the user's knee or elbow.

32. A disposable elastic thermal uniaxial joint wrap according to claim 21 wherein said body portion further comprises at least one slit extending substantially along the longitudinal axis of said body portion enabling said piece of flexible material to stretch transverse to said longitudinal axis of said body portion in order to accommodate bending of the user's knee or elbow.

33. A disposable elastic thermal uniaxial joint wrap according to claim 21 wherein said flexible material further comprises one or more stays to resiliently stiffen said flexible material and thereby minimize bunching of said flexible material when said user's knee or elbow is repeatedly bent.

34. A disposable elastic thermal uniaxial joint wrap according to claim 21 wherein said fastening system is reclosable.

35. A disposable elastic thermal knee wrap according to claim 34 wherein said reclosable fastening system comprises a hook and loop fastening system.

36. A disposable elastic thermal uniaxial joint wrap according to claim 35 wherein said reclosable fastening system comprises a two part hook and loop fastening system.

* * * * *